United States Patent
Hui et al.

(10) Patent No.: US 7,797,038 B2
(45) Date of Patent: Sep. 14, 2010

(54) HEART RATE MONITOR WITH CROSS TALK REDUCTION

(75) Inventors: Chor Kuen Eddy Hui, San Ramon, CA (US); Thomas Ying-Ching Lo, Fremont, CA (US)

(73) Assignee: Salutron, Inc, Fremont, CA (US)

( * ) Notice: Subject to any disclaimer, the term of this patent is extended or adjusted under 35 U.S.C. 154(b) by 327 days.

(21) Appl. No.: 11/835,305

(22) Filed: Aug. 7, 2007

(65) Prior Publication Data

US 2009/0043217 A1 Feb. 12, 2009

(51) Int. Cl.
*A61B 5/04* (2006.01)
(52) U.S. Cl. .................................... 600/519
(58) Field of Classification Search ................ 600/519
See application file for complete search history.

(56) References Cited

U.S. PATENT DOCUMENTS

| | | | | |
|---|---|---|---|---|
| 6,584,344 | B2 * | 6/2003 | Hannula | 600/509 |
| 2007/0118054 | A1 * | 5/2007 | Pinhas et al. | 600/587 |

OTHER PUBLICATIONS

International Search Report and Written Opinion of the International Searching Authority, dated Nov. 7, 2008, PCT Appl. No. PCT/US2008/070560, filed Jul. 18, 2008.
International Preliminary Report dated Feb. 18, 2010 in International Application No. PCT/US2008/070560 filed Jul. 18, 2008.

* cited by examiner

*Primary Examiner*—Carl H Layno
*Assistant Examiner*—Jeremiah T Kimball
(74) *Attorney, Agent, or Firm*—Vierra Magen Marcus & DeNiro LLP (57) ABSTRACT

A heart rate monitor determines a heart rate for a primary subject by reducing noise and cross-talk from unwanted signal transmission sources. A set of pulse peaks having about the same amplitude and an amplitude greater than any other set of peaks are processed to determine a subject's heart rate, while data having an amplitude below that of the set of peaks is ignored. To retrieve enough data to determine a peak amplitude, the signal having heart rate information is sampled at a frequency higher than a normal sampling frequency. In some embodiments, if no data is received for a set time period which is in or above the range, the threshold resets to zero under an assumption that the primary subject is no longer within transmitting range.

29 Claims, 9 Drawing Sheets

Distance a < Distance b

Figure 1

Distance a < Distance b

HEART RATE MONITOR WITH CROSS TALK REDUCTION

BACKGROUND

Use of heart rate monitors has become quite popular during indoor and outdoor recreational exercise. One popular heart rate monitor has a chest strap component and a wrist worn component. The chest strap component contains electrodes which detect an electrocardiogram (EKG) signal for the subject wearing the strap and circuitry which transmits detected signals. The wrist band component receives signals, derives heart rate data from the signal and displays heart rate information derived from the received heart rate data.

In particular, the chest strap portion receives an EKG signal from a subject, amplifies the signal and converts the signal into a pulse. The pulse is modulated by a 5 KHz clock and transmitted wirelessly. Thus, the transmitted signal has a 5 KHz pulse and is typically between five to twenty milliseconds in pulse length. The heart rate receiver module receives modulated signals, demodulates the signals, limits the signals and amplifies the received signal. The amplified signal is then processed to convert the signal back into a digital pulse.

When processing signals in the 5 KHz range, the receiver is prone to receiving considerable amounts of noise and crosstalk. Examples of noise that may be picked up include, for example, fluorescent lighting, vibrations of the subject and surrounding objects, audible noise from audio equipment and other sources, and other energy sources. A receiver may also experience cross-talk between multiple user chest straps. Cross-talk can occur when a receiver picks up signals transmitted by more than one user's chest strap and is undesirable because the receiver picking up two signals has difficulty determining a heart rate for a particular user. In particular, it can be difficult for a monitor to differentiate between a primary subject's signal and unwanted secondary subject signals. Though some chest strap transmitters are encoded, receivers at health clubs and at other locations usually don't recognize encoding. For example, if an exercise machine locked into an encoded chest strap signal, this could prevent subsequent users from utilizing the heart rate monitoring functionality for that exercise machine if they did not have a similarly encoded strap.

Thus, in a club environment for one-way data communication between a transmitter and a receiver, the 5 KHz receivers are generally not made to recognize encoded signals. As a result, the crosstalk is a common problem due to the close proximity between exercise machines and one machine can usually receive signals from multiple near-by heart rate transmitters.

SUMMARY

A heart rate monitor determines a heart rate for a primary subject by reducing cross-talk from unwanted signal transmission sources. Cross-talk is reduced by retrieving enough detail from a received signal to identify the strongest set of peak amplitudes in the signal. The strongest peak amplitudes are associated with the closest transmitter, which is identified as the transmitter of a primary user. Signal data having amplitude values approximately the same as a previous detected maximum peak amplitude are processed to determine a subject's heart rate, while data having an amplitude below the peak level amplitude is ignored. Sets of data peaks having an amplitude less than the highest set of peaks is identified with secondary users and therefore ignored.

In some embodiments, to retrieve enough data to determine a peak amplitude in a signal, the signal having heart rate information is sampled at a frequency at least twice as high as the highest frequency component, and thereby at a higher frequency than a normal sampling frequency for the received signal. For example, in the case of a 5 KHz signal, the sampling rate can be 10 KHz or higher. The higher sampling rate provides more detail in the sampled signal and allows for better differentiation between component frequencies contained in the sampled signal.

To select peaks to process, the present system determines a peak amplitude for a pulse and stores the peak value. Subsequently, only peak data within a small range of the stored value is processed. In some embodiments, if no data is received for a set time period which is in or above the range, the threshold resets to zero under an assumption that the primary subject is no longer within transmitting range.

In one embodiment, the system may determine a heart rate by reducing the cross talk in a signal containing heart rate information for two or more subjects. First, the heart rate monitor receives a signal having heart rate information for two or more subjects. A first peak is identified within a pulse of the signal, the amplitude of the first peak is determined, and a threshold value is then derived from the amplitude of the first peak. The monitor then identifies a second peak within a second pulse of the signal and determines the amplitude of the second peak. The second amplitude is compared to the threshold and a heart rate for a first subject of the two or more subjects is determined using information associated with the second pulse based on the comparison. The heart rate for the first subject is then displayed by the heart rate monitor circuitry of the first exercising apparatus.

This summary is provided to introduce a selection of concepts in a simplified form that are further described below in the description. This summary is not intended to identify key features or essential features of the claimed subject matter, nor is it intended to be used as an aid in determining the scope of the claimed subject matter.

DETAILED DESCRIPTION

A heart rate monitor determines a heart rate for a primary subject by reducing or removing cross-talk from unwanted signal transmission sources in a signal. The cross-talk is reduced by extracting enough detail from a received signal to identify the strongest set of peak amplitudes in the signal. The strongest peak amplitudes are associated with the closest transmitter, which is identified as the transmitter of a primary user. Signal data having peak amplitude values approximately the same as a threshold value are processed to determine a subject's heart rate, while data having an amplitude below the peak level amplitude is ignored. Sets of data peaks having an amplitude less than the highest set of peaks and/or the threshold value are identified with secondary users and not processed while updating the primary subject's heart rate.

To retrieve enough data to determine a peak amplitude, the signal having heart rate information is sampled at a frequency at least twice as the highest frequency component in the received signal. In the case of a 5 KHz signal, the sampling rate can be 10 KHz or higher. The higher sampling rate provides more detail in the sampled signal and allows for better differentiation between component frequencies contained in the sampled signal.

To select peaks to process, the present system determines a peak amplitude for a pulse and stores the peak value. Subsequently, only peak data within a small range of the stored value is processed. In some embodiments, if no data is received for a set time period which is in or above the range, the threshold resets to zero under an assumption that the primary subject is no longer within transmitting range.

The heart rate monitor of the present technology may be implemented with one or more of several technologies, including EKG, infrared, ultrasound, radio frequency and other technologies used to detect heart rate information in a subject. For example, one or more transducers and/or other components and circuitry attached to a chest strap or wrist-worn strap (discussed in more detail below) may incorporate ultrasound, EKG or some other range of signal to detect heart rate information from a subject wearing the strap.

Figure 1:
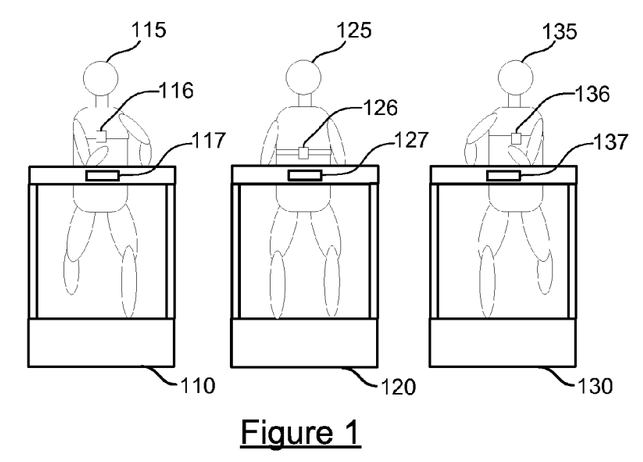
FIG. 1 is an example of an environment which produces cross-talk

FIG. 1 is an example of an environment which produces cross-talk. The environment of FIG. 1 includes exercise machines 110, 120 and 130. Users 115, 125 and 135 are exercising on machines 110-130, respectively. Machine 110 includes heart rate monitoring system receiver 117 incorporated into the machine. Exercise machines 120 and 130 include similar receivers 127 and 137, respectively, built into those respective machines. Additionally, each machine may include additional hardware and/or software for processing received signals, determining a heart rate and reporting the heart rate to a user. An example of hardware and/or software that performs these functions is discussed with respect to FIG. 3. The environment of FIG. 1 may be encountered wherever several exercising machines are used to provide heart rate information, such as fitness clubs, gymnasiums, hospitals, and other locations.

Each of users 115-135 is wearing a transmitter 116, 126 and 136, respectively, for example in the form of a chest strap. Each chest strap includes one or more electrodes and other circuitry. The electrodes and circuitry detect an electrocardiogram (EKG) signal from the user's heart, process the signal and transmit the processed signal to a receiver located on the machine the user is exercising on.

In an environment with several exercising machines such as a health club, machines which receive and process transmitted heart rate signals are often less than two feet away from each other. For example, a health club environment may include several exercise machines 110-130 in the form of treadmills, stationary cycles, or some other machine positioned in a row within the health club. Receivers 117-137 built into the exercise machines may each receive signals from chest straps or other EKG signal transmitters for each of users 115-135 which are within range of each receiver, resulting in cross-talk contained in the signal received by each receiver.

Figure 2A:
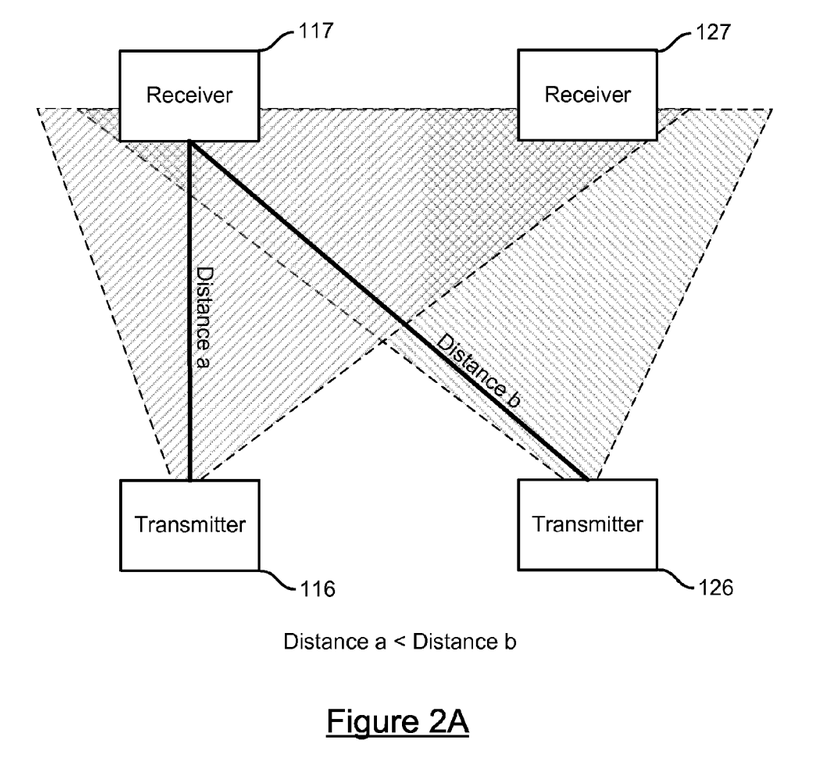
FIG. 2A is a block diagram of an example of receivers and transmitter positioning in a cross-talk environment.

FIG. 2A is a block diagram of an example of receivers and transmitters positioned in a cross-talk environment. The diagram of FIG. 2A provides a simplified top view of the environment of FIG. 1. FIG. 2A includes receiver 117, receiver 127, transmitter 116 and transmitter 126. A shaded transmission field is shown for each transmitter. As illustrated, the signal transmitted by transmitter 116 is received by both receiver 117 and receiver 127. Similarly, the signal transmitted by transmitter 126 is received by receiver 117 and receiver 127. Thus, the signal received by each exercising machine's receiver contains cross-talk from a chest strap transmitter not associated with a user using that machine. The transmission field for different transmitters suitable for use with the present technology may not be shaped in a "cone" as illustrated in FIG. 2A. The shape of the transmission field for each transmitter in FIG. 2A is intended only as an example.

When a receiver is located on an exercise machine such as machine 110, receiver 117 is typically located closer to the transmitter 116 located on user 115 which uses that machine. In particular, the distance from transmitter 116 to receiver 117 is distance A and the distance between transmitter 126 and receiver 117 is distance B. Distances A and B form two sides of a right triangle wherein distance B is the hypotenuse (the longest side of the triangle). As a signal is transmitted through air by each of transmitters 116 and 126, the signal amplitude degrades as it travels. Thus, since distance A is shorter than distance B, the degradation of the signal from transmitter 116 will be less than the degradation of the signal transmitted by transmitter 126 and received by receiver 117. As a result, a signal transmitted by a chest strap of a user 115 exercising on exercise machine 110 will appear to receiver 117 with a higher amplitude than the signal transmitted by transmitter 126 for user 125 on neighboring exercise machine 120.

Figure 2B:
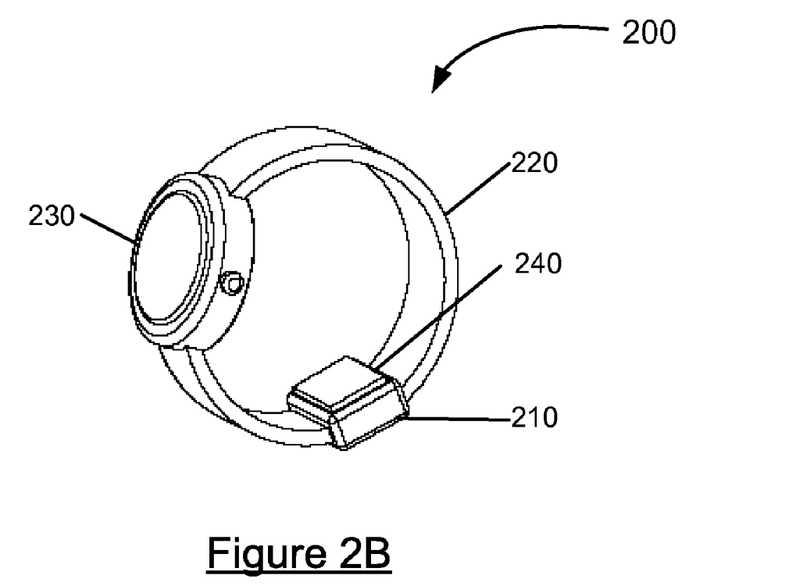
FIG. 2B is an embodiment of a heart rate monitor with a physical connection to a display device.

In addition to an exercise or health club environment, the present technology may be implemented in portable devices as well as stationary exercise machines. FIG. 2B is an embodiment of a heart rate monitor system 200 with a physical connection to a display device. System 200 includes a monitor module 210, a strap 220, a display device 230 and a transmission medium 240. Monitor module 210 detects blood flow through the radial artery at the subject's wrist. Heart rate data is then provided directly to display module 230. In one embodiment, connecting wires are molded into strap 220 between the monitor module 210 and display device 230.

Figure 2C:
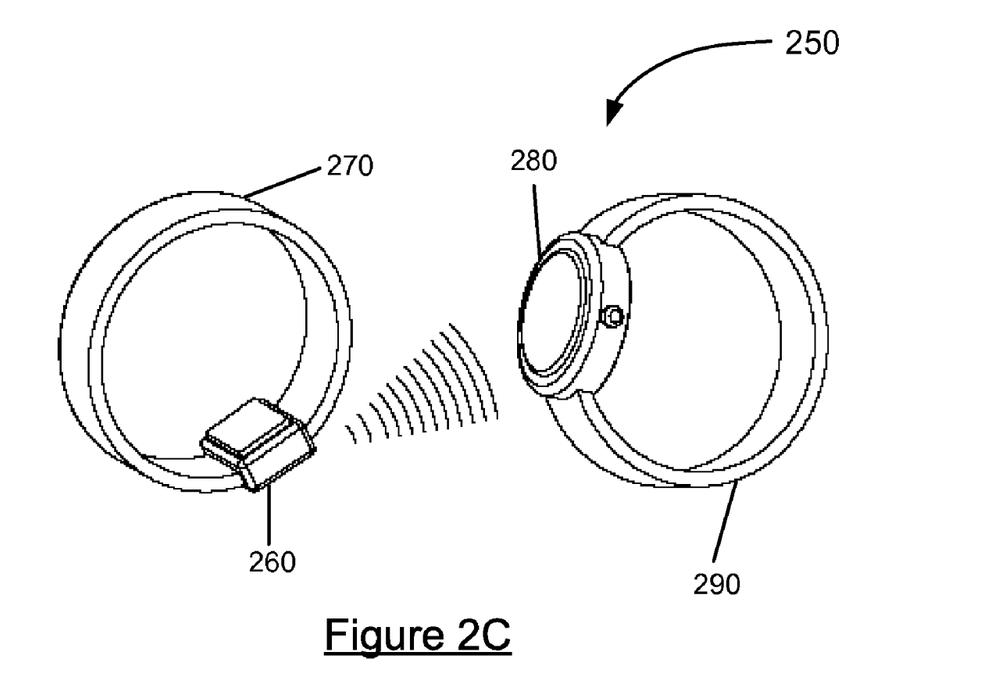
FIG. 2C is an embodiment of an ultrasonic monitor with a wireless connection to a display device.

FIG. 2C is an embodiment of a monitor system 250 which implements a wireless version of a heart rate monitor. The monitor system 250 of FIG. 2C includes monitor module 260, first strap 270 attached to monitor module 260, remote display module 280 and second strap 290 attached to remote display module 280. Monitor modules 210 and 260 detect the blood flow through the radial artery in the wrist. Heart rate data is then provided to display 230 or remote display module 280. Monitor 260 can wirelessly transmit information to a remote display 280 using a wireless transmitter. The remote display 280 may be a monitor screen worn a wrist, incorporated in exercise equipment at a gym or health club or other device and includes a receiver to receive the transmission from monitor 260. The monitor module 260 may be attached to another part of the body (such as the chest over the subject's heart) with a gel pad, biocompatible adhesive or a transmission medium. In some embodiments, the cross-talk reduction techniques utilized and discussed herein may be applied to a system which uses a wrist worn monitor or other portable heart rate monitor and may be useful in reducing cross-talk when a user of the monitoring device is exercising near other signal transmitters or sources of noise.

In some embodiments, the monitor module 260 and strap 270 may be worn on a subject's wrist, chest or other part of their body which may detect heart rate information and the remote display module 280 and second strap 290 may be attached to exercise equipment, for example a portion of a treadmill or a handle bar, cross bar, or other portion of a stationary bicycle. In the example of a stationary bicycle, the cross talk reduction functionality of the present technology may be useful during health club spin classes where several stationary bikes are placed in close proximity together and more than one subject in the class is using a heart rate monitor. The monitor module 260 with strap 270 and remote display module 280 with second strap 290 may also be useful for eliminating cross talk in other indoor and outdoor group sports classes and events, whether the classes or events utilize exercise machines or not.

Figure 3:
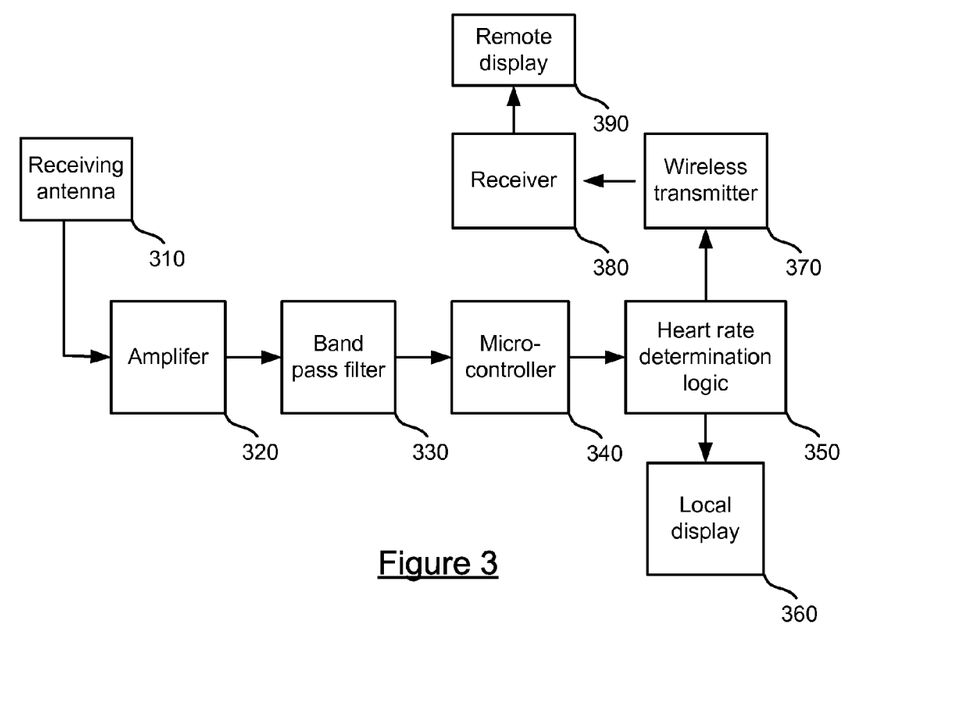
FIG. 3 is a block diagram of an embodiment of a heart rate monitor system.

FIG. 3 is a block diagram of an embodiment of a heart rate monitor system. The system can be implemented on exercising apparatus 110 or monitor systems 200 and/or 250. The heart rate monitor system of FIG. 3 includes receiving antenna 310, amplifier 320, band pass filter 330, microcontroller 340, heart rate determination logic 350, local display 360, wireless transmitter 370, receiver 380 and remote display 390. Receiving antenna 310 receives a signal from a transmitter, such as a chest strap transmitter or similar transmitter.

Amplifier 320 receives a signal from receiving antenna 310 and amplifies the signal by a factor such that the amplified signal can be processed. Band pass filter 330 receives the amplified signal from the amplifier 320, applies a filter to the received signal and provides the filtered signal to microcontroller 340. In some embodiments, the band pass filter may be implemented as several filters. Band pass filter 330 centered at 5 KHz as the carrier frequency may pass a range of frequencies within a received signal, such as a range of 4.5-5.5 KHz, depending on the tolerance of the transmitter used.

Microcontroller 340 reduces and/or removes cross-talk in a received signal by selecting peaks of signal data to process. Microcontroller 340 may be used to implement the methods of FIGS. 6 and 7 discussed in more detail below. Heart rate determination logic 350 receives heart beat candidates in the form of peak data from microcontroller 340 and determines a heart rate from the provided peaks. After determining a heart rate, heart rate information is provided for display to local display 360. In some embodiments, heart rate information may be provided by logic 350 to wireless transmitter 370. Wireless transmitter 370 then modulates the heart rate information, transmits the modulated information to receiver 380, and receiver 380 demodulates and displays the heart rate information through remote displayer 390.

Figure 4:
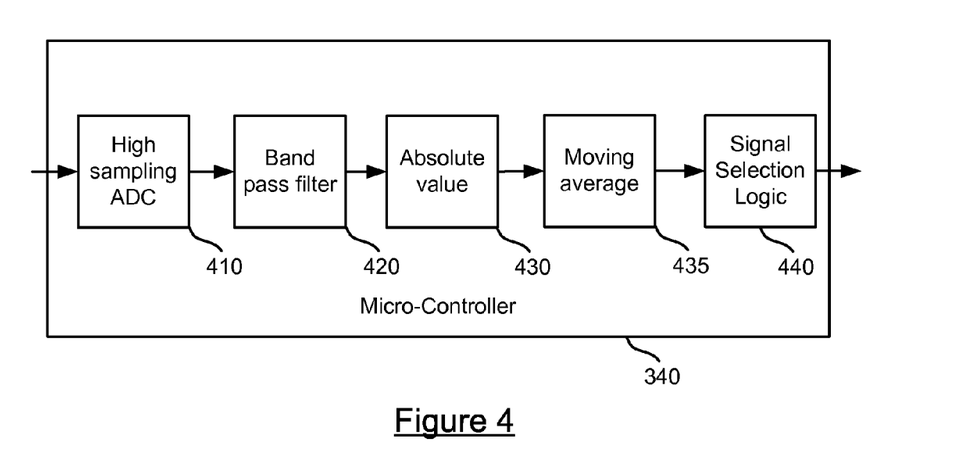
FIG. 4 is a block diagram of an embodiment of a microcontroller.

FIG. 4 is a block diagram of an embodiment of a microcontroller. In some embodiments, the microcontroller of FIG. 4 provides more detail of microcontroller 340 of FIG. 3. Microcontroller 340 includes high sampling analog to digital conversion 410, band pass filter 420, absolute value 430, moving average 435 and signal selection logic 440. The microcontroller receives an analog signal and converts the analog signal to a digital signal using a high sampling rate analog to digital converter 410. Typical systems, including traditional heart rate monitor systems, sample a signal at the minimum required frequency of two times the frequency of the signal being sampled. For example, for a 5 KHz signal, most systems will sample the frequency at 10 KHz (per Nyquist's Rule). However, in some embodiments of the present system, the received signal is sampled at a higher frequency than typical signals, for example, at a sampling rate of 11 KHz or higher for a 5 KHz signal. In some embodiments, the sampling rate is selected based on the tolerance of the transmitter used.

Band pass filter 420 receives the digitized signal and applies filters to the signal. Band pass filter 420 may remove harmonics, and/or other noise and unwanted elements which may result from the sampling. Absolute value module 430 generates an absolute value for the filtered signal. In some embodiments, the absolute value is taken by squaring the value of the filtered signal. The signal is then processed to determine a moving average by moving average logic 435 and provided to signal selection logic 440. Signal selection logic 440 receives the signal and selects peaks in the signal associated with a primary subject. This is discussed in more detail below.

Figure 5:
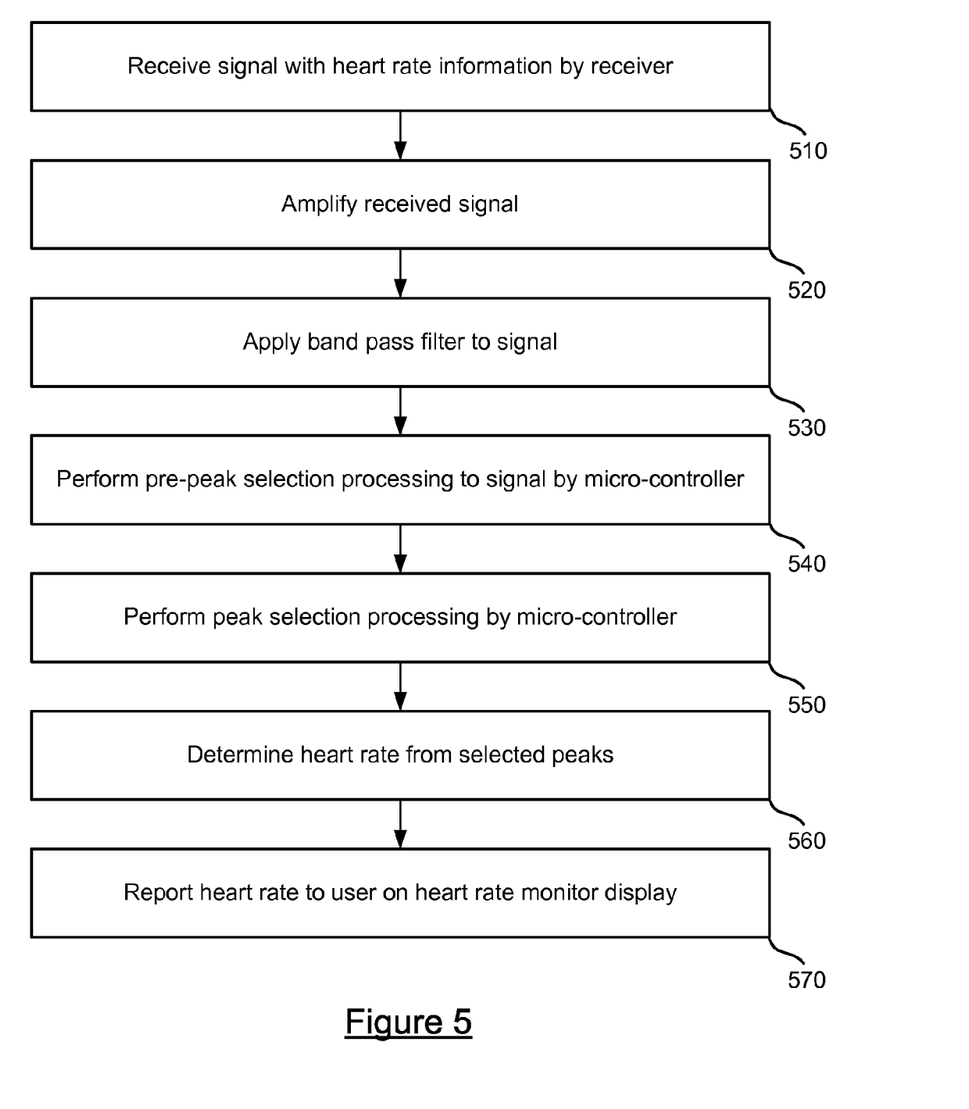
FIG. 5 is a flowchart of an embodiment of a method for reporting a heart rate of a user.

FIG. 5 is a flowchart of an embodiment of a method for reporting a heart rate of a user. In some embodiments, the method of FIG. 5 is implemented by the system of FIG. 3.

First, a signal is received with heart rate information via a receiver at step 510. With respect to the system of FIG. 3, the signal may be received by receiving antenna 310. The signal may contain data transmitted from one or more users 110-130, noise, music interference from a speaker, machines 110-130, or other source an/or contain other unwanted noise or signal elements. Next, the received signal is amplified at step 520. The signal may be amplified by amplifier 320 by a factor that allows it to be processed by the remainder of the system.

A band pass filter is applied to the amplified signal at step 530. The band pass filter helps reduce noise and other wanted signal component and may be implemented by band pass filter 330 of the system of FIG. 3.

Steps 540-550 may be performed by microcontroller 340 of the system of FIG. 3. Pre-peak selection processing is performed on a signal by microcontroller 340 at step 540. The pre-peak selection processing may include analog to digital conversion, filtering the digitized signal, determining the absolute value of the signal and calculating a moving average of the signal. Performing pre-peak selection processing is discussed in more detail below with respect to the method of FIG. 6.

Peak selection processing is then on the signal by microcontroller 340 at step 550. Peak selection processing may include identifying the highest peak amplitude and processing only subsequent peaks with the same or similar range of amplitude. Other data not within the determined range is either discarded or identified as a new primary user. Peaks that are selected for processing are considered heart beat candidates. Performing peak selection processing is discussed in more detail below with respect to FIG. 7A.

A heart rate is determined from selected peaks at step 560. The selected peaks are processed to confirm they are true heartbeats. Once confirmed, a heart rate is updated with the timing information for the true heart beats. After determining the heart rate, the heart rate information is reported to a user on a heart rate monitor display at step 570. The information may be reported through local display 360, remote display 390, a display incorporated into or in communications with exercise machines such as machines 110-130, or some other display device.

Figure 6:
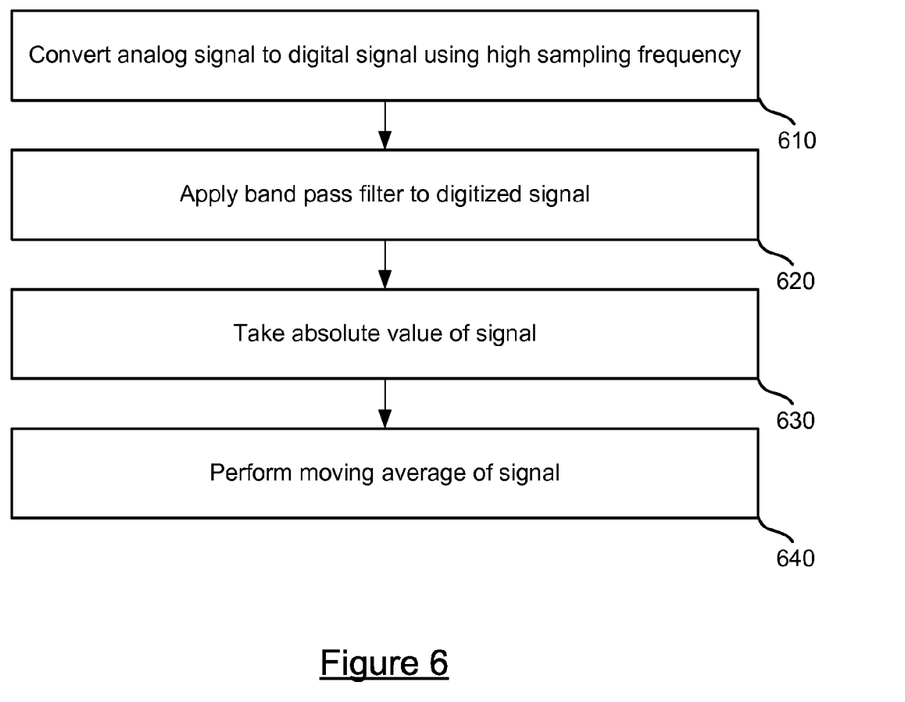
FIG. 6 is a flowchart of an embodiment of a method for performing pre-signal selection processing.
Figure 7A:
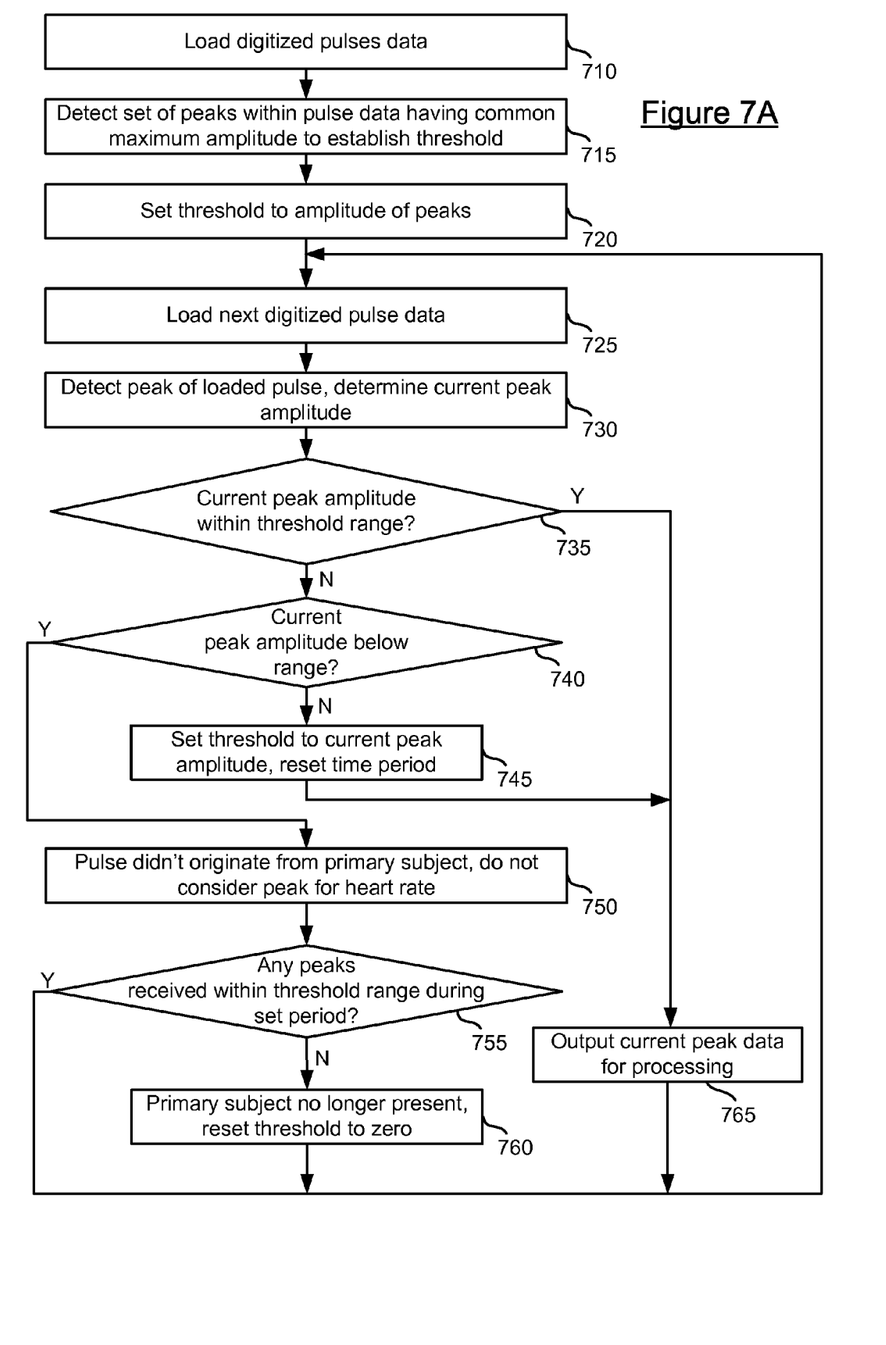
FIG. 7A is a flowchart of an embodiment of a method for performing peak selection.

FIG. 6 is a flowchart of an embodiment of a method for performing pre-peak selection processing. In some embodiments, the method of FIG. 6 provides more detail for step 540 of the method of FIG. 5 and is performed by microcontroller 340 of the system of FIG. 3. First, analog signals are converted to digital signals using a high sampling frequency at step 610. Typical analog to digital conversion samples at a rate of twice the highest frequency component in the signal being sampled. In the present system, higher sampling rates are used to retrieve more information from the sampled signal, such as different sources of pulse data, peak amplitudes and other signal data. For example, for a 5 KHz signal, sampling may be performed at 10 KHz or faster. In some embodiments, other sampling rates may be used as well, including a rate which is more than twice the signal frequency being sampled, such as 11 KHz or faster.

After converting the signal to a digital signal, a band pass filter is applied to the digitized signal at step 620. The band pass filter may remove noise, harmonics and other effects of the analog to digital conversion. Next, the absolute value of the signal is taken in step 630. In some embodiments, the absolute value is determined by squaring the filtered signal by absolute value module 430 of microcontroller 340. Next, the moving average of the signal is performed at step 640. The moving average is taken to remove high frequency components of the signal and may be performed in several ways as known in the art.

FIG. 7A is a flowchart of an embodiment of a method for performing peak selection. In some embodiments, the method of FIG. 7A provides more detail for step 550 in the method of FIG. 5 and is performed by signal detection logic 440 of microcontroller 340.

A first digitized pulse of data is loaded at step 710. The digitized pulse may be generated as a result of performing pre-peak selection processing at step 540. The pulse will typically have several pulse peaks having different amplitudes, representing signals received from different sources, such as user of one or more exercising machines 110-130.

Next, a minimum number of pulses having a maximum amplitude are detected at step 715. The minimum number of pulses having a maximum amplitude is required to be detected before determining a threshold to compare to subsequent pulses. In some embodiments, a peak amplitude of a single pulse may be used to set the threshold. In this case, the threshold is based on the peak amplitude of the first pulse received by the system. In some embodiments, the threshold is based on a set of pulses having a minimum number of pulses and about the same peak amplitude where no other set of pulses has the required number of pulses and a common peak amplitude that is greater than the set on which the threshold is based on. Determining a minimum number of pulses having a maximum amplitude is discussed in more detail below with respect to FIG. 7B.

In some embodiments, the digitized pulse peak is detected as the highest data point within the pulse. In some embodiments, one or more waveforms for the sampling points are generated and the highest peak in the generated waveform is selected as the highest peak. For example, if the data points of the digitized pulse signal indicate that the pulse includes two or more sinusoidal wave, the highest peak of the sinusoidal waves is selected as the peak whether an actual data point is associated with the peak or not.

A threshold is set to the value of the peak amplitude at step 720. This initial value of the threshold is set based on the first digitized pulse processed by the system. The threshold will be used later to determine if subsequent peaks are associated with the same source (the primary user) as that used to generate the threshold. The next digitized pulse is then loaded at step 725. The peak of the currently loaded pulse is detected and the amplitude of the current peak is determined at step 730. Detecting the peak and the amplitude of the peak at step 730 is performed in a similar manner as in step 715.

A determination is made as to whether the current peak amplitude is within a range of the threshold at step 735. In some embodiments, the system determines whether the current pulse originated from the same source (the primary user) as the previously highest peak. If the current peak amplitude is within a set threshold range, then the current peak and previous highest peak are from the same transmitter and associated with the primary user. If the current peak is not within the threshold, then either the current peak or the previous highest peak is not associated with the primary user. In some embodiments, a range for the threshold may be set to 3-5 percent greater and less than the threshold. For example, the determination may determine whether the current peak amplitude is within plus or minus three to five percent of the threshold set at step 720. If the current peak amplitude is not within the defined threshold range, the method of FIG. 7A continues to step 740. If the current peak amplitude is within the defined threshold range, the method of FIG. 7A continues to step 765 where the peak is determined to be associated with the primary user and the current peak data is output for processing. The current peak data is output for processing to heart rate determination logic 350 by microcontroller 340.

A determination is made as to whether the current peak amplitude is below the set threshold range at step 740. This determination is made to determine whether the peak is associated with a new primary user, a secondary user or noise. If the current peak amplitude is not below the set threshold range, the current peak amplitude is above the range and the threshold is set to the current peak amplitude at step 745. Additionally, a time period for determining whether the primary user has left is reset at step 745. After the threshold is set to the current peak amplitude and the time period is reset, the method of FIG. 7A continues to step 765. Because the current peak is determined to be above the range it is now considered to be associated with a new primary user. The threshold is changed so that only peaks of similar amplitude are processed into the subject's heart rate.

In some embodiments, a new threshold will not be set unless the current peak amplitude is determined to exceed the set threshold range multiple times. This prevents the threshold from being increased by mistake due to an error or a spurious noise and limiting the ability of the system to detect a heart rate from the actual user's transmitted signal. In this embodiment, rather than setting the threshold with the first higher peak amplitude at step 745, a counter is implemented and checked at step 745 to see if the required number of detections have been detected. At step 745, if the counter value indicates a certain number of detected peak amplitudes have exceeded the set range for the threshold (such as three counts), then the threshold may be set to the current peak amplitude.

If the current peak amplitude is determined to be below the range, the method of FIG. 7A continues to step 750 where the system determines that the pulse did not originate from the primary subject and does not consider the current peak determining for the subject's heart rate at step 750. In this case, the pulse is associated with a secondary user, noise or some other component or source. The method of FIG. 7A then continues to step 755.

A determination is made as to whether any peaks have been received within the threshold range during a set period at step 755. This determination is a mechanism for resetting the threshold in case the primary user is no longer within range of the exercise machine, wrist worn monitor or other device detecting and determining a user's heart rate and prevents the system being permanently locked at a particular peak amplitude value. In some embodiments, the set period may be a time period of three seconds, however other time period may be used. If no peaks have been received within the threshold range during the set time period, a determination is made that the primary subject is no longer present and the threshold is reset to zero at step 760. By resetting the threshold, the next detected digitized pulse will be used to set the next threshold. The method of FIG. 7A then returns to step 725. If one or more peaks have been received within the threshold range during the set time period, the method of FIG. 7A returns to step 725 without resetting the threshold to zero.

Figure 7B:
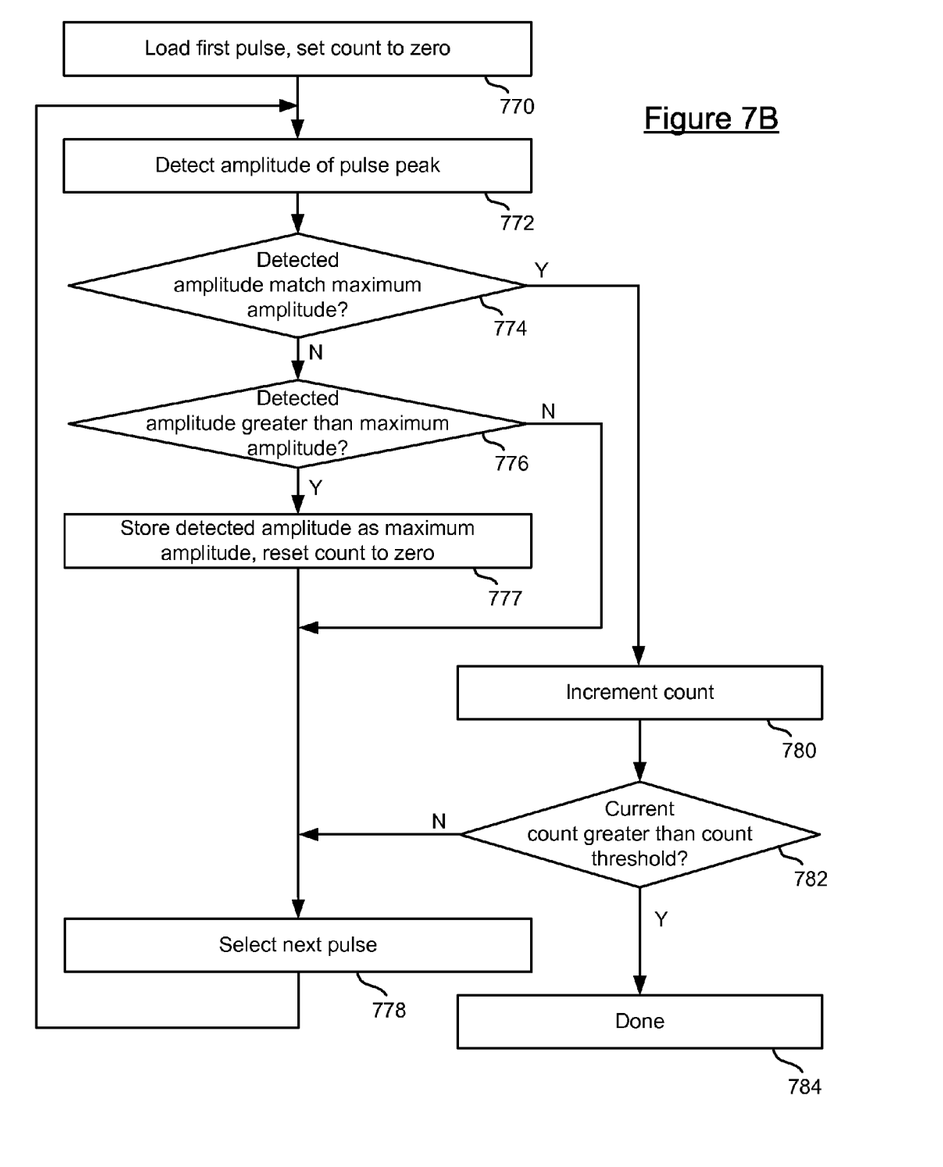
FIG. 7B is a flowchart of an embodiment of a method for establishing a peak threshold.

FIG. 7B is a flowchart of an embodiment of a method for detecting a set of peaks within pulse data where the peaks have common maximum amplitudes to establish a threshold. In some embodiments, the method of FIG. 7B provides more detail for step 715 of the method of FIG. 7A. First, a first pulse is loaded and the count is set to zero at step 770. The count is used to determine the minimum number of peaks set used to establish a threshold. Next, the amplitude of the pulse peak is detected at step 772. A determination is then made as to whether the detected amplitude matches a maximum amplitude. If no maximum amplitude has been stored yet (such as the case for making the determination for the first pulse), the peak of the pulse considered is set to the maximum amplitude and the determination of step 774 is considered answered in the affirmative.

If the detected amplitude matches the maximum amplitude, the count is incremented at step 780. A determination is then made as to whether the current count is greater than the count threshold at step 782. The count threshold may be a parameter set by a user, by a manufacturer, determined over time based on use of the monitor, or a combination of these methods. For example, a monitor system of the present technology may have a threshold of three set by the manufacturer, but the threshold may be adjusted by a user. If the current count is greater than the threshold, the method of FIG. 7B ends a step 784. If the current count is not greater than the threshold, then the next pulse is selected at step 778 and the method returns to step 772.

If the detected amplitude does not match the maximum amplitude at step 774, a determination is made as to whether the detected amplitude is greater than the maximum amplitude at step 776. If the detected amplitude is not greater than the maximum amplitude, then the peak has an amplitude lower than that of the set and the method continues to step 778 where the next pulse is detected. If the detected amplitude is greater than the maximum amplitude, then the detected amplitude is stored as the maximum amplitude and the count is reset to zero at step 777. Next, the next pulse is selected at step 778 and the method of FIG. 7B returns to step 772.

Figure 8:
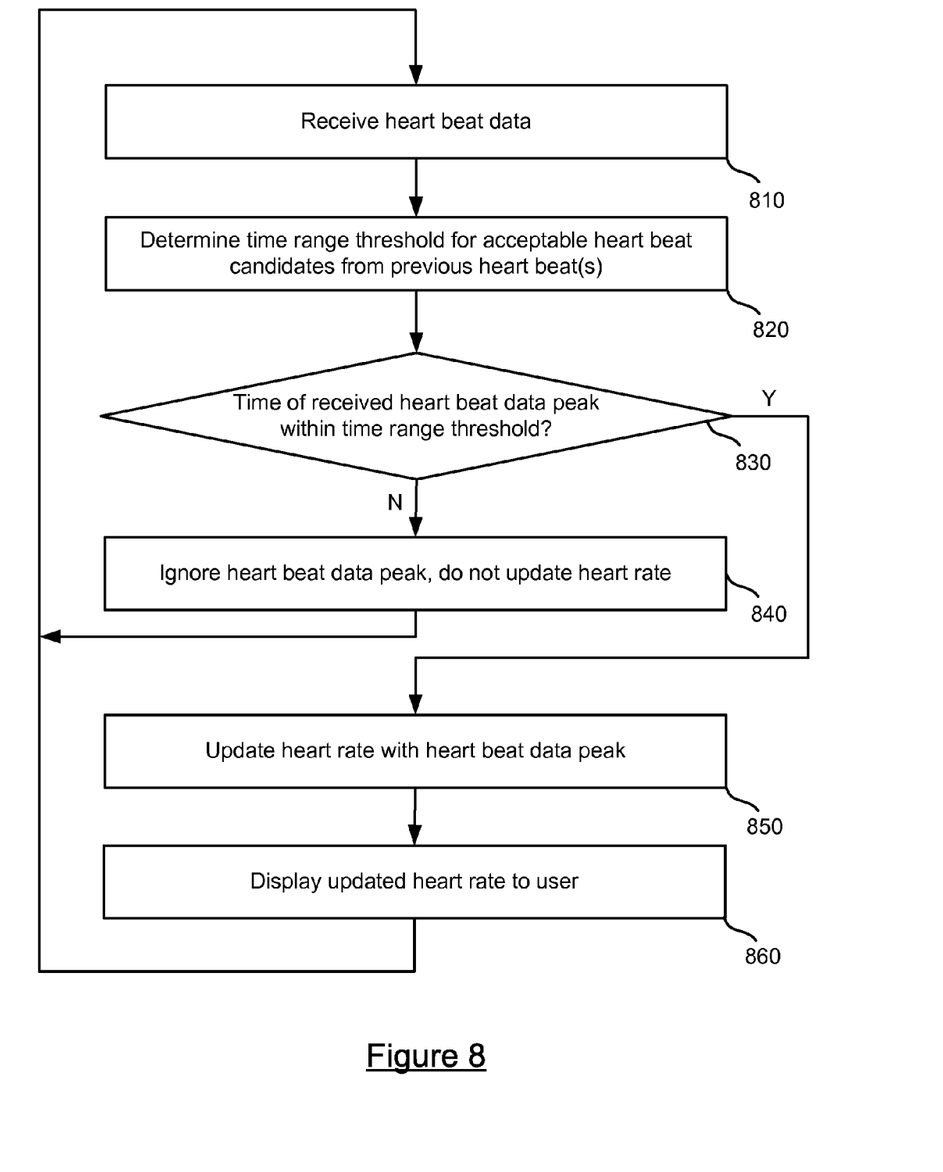
FIG. 8 is a flowchart of an embodiment of a method for determining a heart rate from a selected peak.

FIG. 8 is a flowchart of an embodiment of a method for determining a heart rate from a selected peak. In some embodiments, FIG. 8 provides more detail for step 560 and is implemented by heart rate determination logic 350. First, heartbeat data is received at step 810. The heartbeat data is received by logic 350 from microcontroller 340 and includes peak information at step 765. Next, a time range threshold for an acceptable heartbeat candidate is determined from previous heartbeats at step 820. In some embodiments, this determination limits the range of timing for a heartbeat based on the current heart rate. Thus, if a current heart rate for a user 170 heartbeats per minute, subsequent heartbeat candidates may only be considered a true heart beat if the resulting heart rate based on that received heartbeat is within plus or minus three percent of the current heart rate. For example, for a current heart rate of 170 beats per minute, beats must be within five beats (3% of 170 beats) of the current rate, or 165-175 beats per minute. In some embodiments, other ranges may be used as well, including static percentage ranges and dynamic ranges that vary based on the current heart rate and/or other information.

A determination is then made as to whether the timing of the received heartbeat peak data is within a time range threshold at step 830. As discussed above with respect to step 820, the heartbeat peak data must be within a time range threshold in order to be considered a true heartbeat. If the timing of the received heartbeat peak data is within the time range threshold, the peak heartbeat data is considered a true heartbeat and the heart rate is updated with the heartbeat peak data at step 850. If the timing of the received heartbeat peak data is not within the time range, the heartbeat peak data is ignored and not used to update the heart rate at step 840. The method of FIG. 8 then returns from step 840 to step 810 and awaits the next heartbeat peak data.

After updating the heart rate with the heartbeat peak data, the heart rate information is provided to a user through display at step 860. The heart rate information may be provided to a user through local display 360, remote display 390, or some other display.

Figure 9:
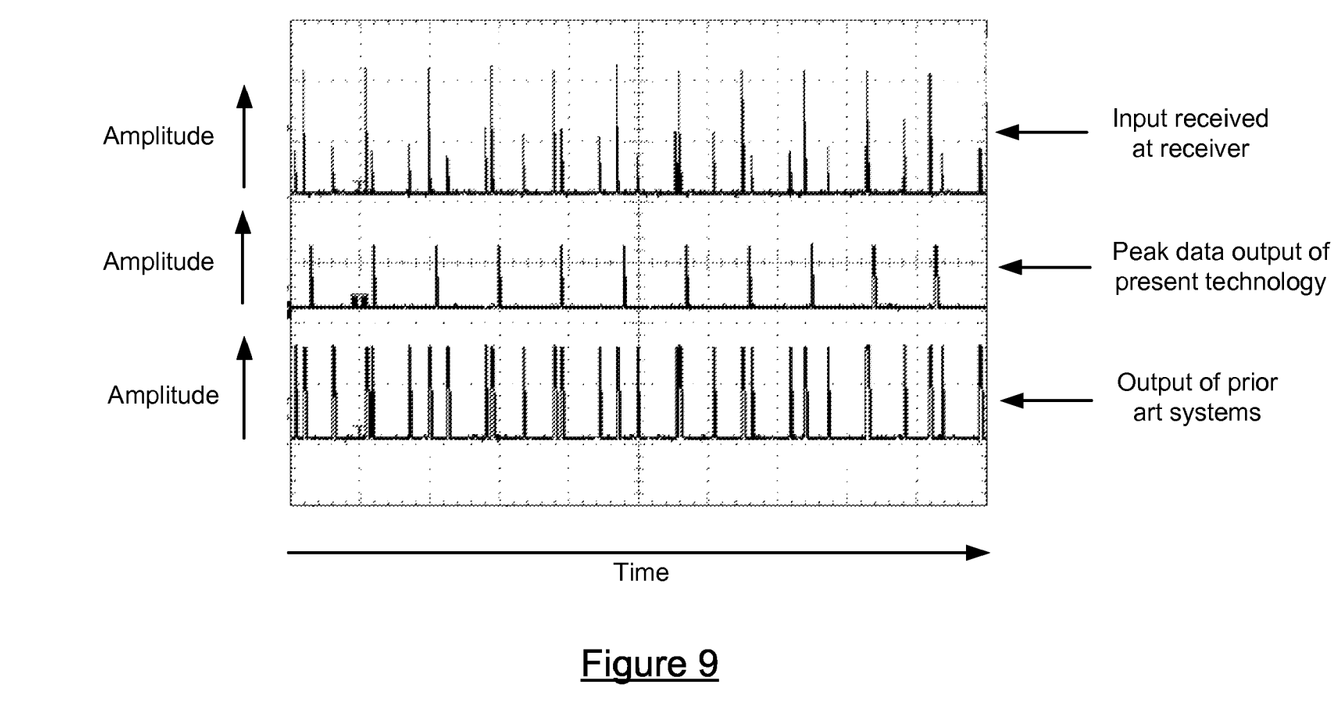
FIG. 9 is an example of an input signal with heart rate information in results of processing the input signal.

FIG. 9 is an example of three signals encountered within a heart rate monitor which contain heart rate information. The signals are illustrated on a grid in which the horizontal axis is time and a vertical axis for each signal showing signal amplitude. The first signal illustrates an input signal received at receiving antenna 310. As illustrated, the received signal has multiple amplitudes or bursts of data with several different bursts at three or more different levels of amplitude. The groupings by amplitude suggest that each amplitude group is associated with a user at a different distance away from the current receiver. The second signal indicates a peak data output of the present technology. As illustrated, peaks are only illustrated in the second signal for corresponding peaks in the input signal that have the highest amplitude. The slight delay in timing between the first and the second signals is due to the software processing time. The third signal illustrates an output of a traditional system. This traditional system output shows that a pulse is generated for each and every pulse contained in the input received at the receiver. Each pulse generated in the traditional system output has a uniform amplitude, thus making it difficult to discern from which user or what location the particular pulse is associated with.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claims appended hereto.

We claim:

1. A computer implemented method for determining a heart rate, comprising:

receiving wireless signals at a heart rate monitor, the wireless signals containing heart rate information of a primary user and at least one secondary user, the heart rate information of the at least one secondary user is unwanted cross-talk;

identifying a peak associated with one pulse of the wireless signals;

determining an amplitude of the peak associated with the one pulse;

deriving a threshold value from the amplitude of the peak associated with the one pulse;

identifying a peak associated with another pulse of the wireless signals;

determining an amplitude of the peak associated with the another pulse;

comparing the amplitude of the peak associated with the another pulse to the threshold value;

determining a heart rate of the primary user using information associated with the another pulse based on said step of comparing; and displaying the heart rate of the primary user at the heart rate monitor.

2. The computer implemented method of claim 1, further comprising:

sampling the wireless signals at the heart rate monitor at a sampling frequency of between 10 KHz and 20 KHz, before the identifying the peak associated with the one pulse of the wireless signals and the identifying the peak associated with the another pulse of the wireless signals.

3. The computer implemented method of claim 2, wherein the sampling frequency is between 11 KHz and 15 KHz.

4. The computer implemented method of claim 1, wherein the wireless signals are received at the heart rate monitor from transmitters worn by the primary user and the at least one secondary user, the transmitters are within transmission range of the heart rate monitor.

5. The computer implemented method of claim 1, wherein the threshold value is in a range derived from the amplitude of the peak associated with the one pulse.

6. The computer implemented method of claim 1, wherein said step of determining a heart rate includes:

updating a current heart rate based on timing information for an occurrence of the peak associated with the another pulse.

7. The computer implemented method of claim 1, wherein:

the wireless signals include a number of peaks having a similar maximum amplitude; and the threshold value is set based on the similar maximum amplitude.

8. The computer implemented method of claim 1, wherein said step of determining a heart rate includes:

determining that a time between the peak associated with the one pulse and the peak associated with the another pulse is within a time range threshold which is based on a current heart rate.

9. The computer implemented method of claim 1, wherein said step of determining a heart rate includes:

determining that the amplitude of the peak associated with the another pulse is less than the threshold value; and not updating the heart rate using the peak associated with the another pulse.

10. The computer implemented method of claim 1, wherein said step of determining a heart rate includes:

determining that the amplitude of the peak associated with the another pulse is greater than the threshold value; and revising the threshold value based on the amplitude of the peak associated with the another pulse.

11. The computer implemented method of claim 1, wherein one or more signal pulses which are in the wireless signals and which have peak amplitudes less than the threshold value are not used to determine the heart rate.

12. The computer implemented method of claim 1, wherein the heart rate monitor is incorporated into an exercising apparatus which is used by the primary user.

13. The computer implemented method of claim 1, wherein the wireless signals include a wireless signal from a transmitter worn by the primary user, and the heart rate monitor does not recognize the transmitter by encoding of the wireless signals.

14. The computer implemented method of claim 1, wherein:

the wireless signals are received from first and second transmitters, the first transmitter is part of an apparatus worn by the primary user which converts an EKG signal of the primary user into the one pulse, and the second transmitter is part of an apparatus worn by the at least one secondary user which converts an EKG signal of the at least one secondary user into the another pulse.

15. The computer implemented method of claim 1, wherein:

the one pulse and the another pulse each are modulated at 5 KHz and are between five to twenty milliseconds in length.

16. The computer implemented method of claim 1, further comprising:

processing the wireless signals by sampling, obtaining an absolute value, and obtaining a moving average, before the identifying the peak associated with the one pulse of the wireless signals and the identifying the peak associated with the another pulse of the wireless signals.

17. The computer implemented method of claim 1, wherein the wireless signals are not encoded based on a transmitter.

18. A computer implemented method for determining a heart rate, comprising:

receiving wireless signals at heart rate monitor circuitry, the wireless signals containing heart rate information of a primary user and heart rate information of at least one secondary user, the heart rate information of the at least one secondary user is unwanted cross-talk;

identifying one set of peaks associated with the wireless signals;

determining a highest-amplitude peak within the one set of peaks;

deriving a threshold value from an amplitude of the highest-amplitude peak within the one set of peaks;

identifying a subsequent peak associated with the wireless signals, the subsequent peak is after the one set of peaks;

determining an amplitude of the subsequent peak;

comparing the amplitude of the subsequent peak to the threshold value;

determining whether to update a heart rate of the primary user based on said step of comparing; and displaying the heart rate of the primary user using the heart rate monitor circuitry.

19. The computer implemented method of claim 18, wherein the threshold value is in a range of threshold values which is based on the highest-amplitude peak within the one set of peaks.

20. The computer implemented method of claim 18, wherein said step of determining a heart rate includes:

updating the heart rate based on timing information for an occurrence of the subsequent peak.

21. The computer implemented method of claim 18, wherein said step of determining whether to update the heart rate includes:

determining whether a time between the highest-amplitude peak and the subsequent peak is within a time range threshold;

wherein the heart rate is updated using the subsequent peak when the time between the highest-amplitude peak and the subsequent peak is determined to be within the time range threshold, and the heart rate is not updated using the subsequent peak when the time between the highest-amplitude peak and the subsequent peak is determined to be outside the time range threshold.

22. The computer implemented method of claim 18, wherein said step of determining whether to update the heart rate includes:
   comparing the amplitude of the subsequent peak to the threshold value;
   wherein the heart rate is updated using the subsequent peak when the amplitude of the subsequent peak is determined to exceed the threshold value, and the heart rate is not updated using the subsequent peak when the amplitude of the subsequent peak is determined to be less than the threshold value.

23. The computer implemented method of claim 18, wherein said step of determining a heart rate includes:
   determining that the amplitude of the subsequent peak is greater than the threshold value; and
   updating the threshold value based on the amplitude of the subsequent peak in response to determining that the amplitude of the subsequent peak is greater than the threshold value.

24. The computer implemented method of claim 18, wherein one or more signal portions which are in the wireless signals and which have peak amplitudes less than the threshold value are not used to determine the heart rate.

25. The computer implemented method of claim 18, further comprising:
   processing the wireless signals by sampling, obtaining an absolute value, and obtaining a moving average, before the identifying the highest-amplitude peak and the identifying the subsequent peak.

26. The computer implemented method of claim 18, wherein:
   the wireless signals include a wireless signal from a transmitter which is worn by the primary user, and a wireless signal from a transmitter which is worn by the at least one secondary user.

27. The computer implemented method of claim 18, wherein:
   the heart rate monitor circuitry is incorporated into an exercising apparatus which is used by the primary user.

28. The computer implemented method of claim 18, wherein:
   the wireless signals include pulses modulated at 5 KHz and between five to twenty milliseconds in length.

29. The computer implemented method of claim 18, wherein:
   the subsequent peak is identified as a highest-amplitude peak within a subsequent set of peaks which is after the one set of peaks.

\* \* \* \* \*